United States Patent
Lian et al.

(10) Patent No.: US 9,456,759 B2
(45) Date of Patent: Oct. 4, 2016

(54) DEVICE FOR AUTOMATIC MAPPING OF COMPLEX FRACTIONATED ATRIAL ELECTROGRAM

(71) Applicant: BIOTRONIK SE & Co. KG, Berlin (DE)

(72) Inventors: Jie Lian, Beaverton, OR (US); Christopher S. de Voir, Tigard, OR (US)

(73) Assignee: BIOTRONIK SE & CO. KG, Berlin (DE)

(*) Notice: Subject to any disclaimer, the term of this patent is extended or adjusted under 35 U.S.C. 154(b) by 17 days.

(21) Appl. No.: 14/468,267

(22) Filed: Aug. 25, 2014

(65) Prior Publication Data

US 2015/0080752 A1 Mar. 19, 2015

Related U.S. Application Data

(60) Provisional application No. 61/878,052, filed on Sep. 16, 2013.

(51) Int. Cl.
*A61B 18/12* (2006.01)
*A61B 18/14* (2006.01)
(Continued)

(52) U.S. Cl.
CPC ........... *A61B 5/04011* (2013.01); *A61B 5/042* (2013.01); *A61B 5/04012* (2013.01);
(Continued)

(58) Field of Classification Search
CPC .. A61B 5/0452; A61B 5/0456; A61B 5/046; A61B 2018/00577; A61B 18/1492
USPC ................. 600/509, 516; 606/32, 33, 41
See application file for complete search history.

(56) References Cited

U.S. PATENT DOCUMENTS

| 5,891,048 A | 4/1999 | Nigam et al. |
| 7,904,143 B2 | 3/2011 | Ishay |

(Continued)

FOREIGN PATENT DOCUMENTS

| EP | 2179690 A1 | 4/2010 |
| WO | 2012/021022 | 2/2012 |

OTHER PUBLICATIONS

El Haddad, Milad et al. "Histogram Analysis: A Novel Method to Detect and Differentiate Fractionated Electrograms During Atrial Fibrillation". Journal of Cardiovascular Electrophysiology; Jul. 2011, vol. 22 Issue 7, p. 781-790, 10p.*

(Continued)

*Primary Examiner* — Allen Porter, Jr.
(74) *Attorney, Agent, or Firm* — ARC IP Law, PC; Joseph J. Mayo

(57) ABSTRACT

A device that monitors and evaluates electrogram signals representing electric activities of a heart chamber, and includes a signal input connected to a mapping catheter, and a signal processing and evaluation unit. The mapping catheter includes one or more electrode poles that pick up electric potentials and generate electrogram signals therefrom. When an electrogram signal is received by the signal input, the signal processing and evaluation unit identifies waveform deflections in the electrogram signal, measures deflection intervals between each pair of consecutive deflection complexes in the electrogram signal, measures at least one metric that characterizes a morphology of a deflection complex in the electrogram signal, generates a multi-dimensional deflection vector of at least two dimensions for each identified deflection, determines a distance between each pair of consecutive deflections from the multi-dimensional deflection vectors, and determines a cumulative distance between deflections in a time window of predetermined length.

13 Claims, 6 Drawing Sheets

(51) Int. Cl.
    A61B 5/04      (2006.01)
    A61B 5/042     (2006.01)
    A61B 5/0452    (2006.01)
    A61B 5/046     (2006.01)
    A61B 18/00     (2006.01)
(52) U.S. Cl.
    CPC ......... *A61B5/0452* (2013.01); *A61B 18/1492* (2013.01); *A61B 5/046* (2013.01); *A61B 2018/00577* (2013.01); *A61B 2018/00839* (2013.01); *A61B 2018/00904* (2013.01)

(56) References Cited

U.S. PATENT DOCUMENTS

| | | | | |
|---|---|---|---|---|
| 8,315,696 | B2* | 11/2012 | Schwartz | A61B 5/0422 600/509 |
| 2005/0171447 | A1 | 8/2005 | Esperer | |
| 2006/0247547 | A1 | 11/2006 | Sarkar et al. | |
| 2007/0197929 | A1 | 8/2007 | Porath | |
| 2010/0004550 | A1* | 1/2010 | Ishay | A61B 5/042 600/515 |
| 2013/0253349 | A1* | 9/2013 | Hayam | A61B 5/046 600/509 |

OTHER PUBLICATIONS

Nademanee et al., "A New Approach for Catheter Ablation of Atrial Fibrillation: Mapping of the Electrophysiologic Substrate", a publication of the Journal of the American College of Cardiology (JACC) 2004, vol. 43 pp. 2044-2053; US and Thailand.

Lau et al., "Stability of Complex Fractionated Atrial Electrograms", a publication of the Journal of Cardiovascular Electrophysiology 2012, vol. 23 pp. 980-987; Netherlands.

Grzeda et al., "Complex Fractionated Atrial Electrograms: Properties of Time-Domain Versus Frequency-Domain Methods", a publication of the Heart Rhythm Journal 2009, vol. 6 pp. 1475-1482; US.

Ciaccio et al., "Differences in Repeating Patterns of Complex Fractionated Left Atrial Electrograms in Longstanding Persistent as Compared with Paroxysmal Atrial Fibrillation", a publication of the Circulation: Arrhythmia and Electrophysiology Journal 2011, vol. 4 pp. 470-477; New York, US.

Ng et al., "Measuring the Complexity of Atrial Fibrillation Electrograms", a publication of the Journal of Cardiovascular Electrophysiology 2010, vol. 21 pp. 649-655; US.

Lin et al., "Novel Assessment of Temporal Variation in Fractionated Electrograms Using Histogram Analysis of Local Fractionation Interval in Patients with Persistent Atrial Fibrillation", a publication of the Circulation: Arrhythmia and Electrophysiology Journal 2012, vol. 5 pp. 949-956; Taiwan.

Lee et al., "Relationship Among Complex Signals, Short Cycle Length Activity, and Dominant Frequency in Patients with Long-Lasting Persistent AF" published in the Heart Rhythm Journal 2011, vol. 8 pp. 1714-1719; Melbourne, Australia.

European Search Report received from EP Application Serial No. 14183365, dated Feb. 23, 2015, 9 pages.

Mayank Kumar, et al., "Computerized Detection & Classification of ECG Signals", Emerging Trends in Electrical Engineering and Energy Management, Dec. 13, 2012, ICETEEEM-2012, pp. 126-130, India.

* cited by examiner

DEVICE FOR AUTOMATIC MAPPING OF COMPLEX FRACTIONATED ATRIAL ELECTROGRAM

This application claims the benefit of U.S. Provisional Patent Application 61/878,052 filed on 16 Sep. 2013, the specification of which is hereby incorporated herein by reference.

BACKGROUND OF THE INVENTION

1. Field of the Invention

Embodiments of the invention generally relate to a device that monitors and evaluates electrogram signals that represent electric activities of a heart chamber or intracardiac electrograms, such as atrial intracardiac electrograms.

2. Description of the Related Art

Intracardiac electrograms may be picked up by electrode leads or catheters that include one or more electrode poles that pick up electric potentials originating from the myocardium of a respective heart chamber (atrium or ventricle). Typically, myocardial cells depolarize and contract in response to natural or artificial stimulation. In a healthy heart chamber, depolarization of the muscle cells of the myocardium occurs nearly simultaneously leading to a contraction of the respective heart chamber. The change of electric potentials that co-occur with the depolarization and repolarization may be picked-up and form time-varying electrograms. In a certain time period after depolarization a muscle cell is unsusceptible for another stimulation. The time period is typically called refractory period of the muscle cell. In a healthy heart, electric conduction of stimulation pulses causes the myocardium to contract in a coordinated manner. However, if the electric conduction is affected, an uncoordinated contraction of muscle cells may occur wherein a part of the muscle cells contract while others already are refractory and become stimulated with a certain delay, which may lead to fibrillation of the affected heart chamber, for example AF (atrial fibrillation).

A means to prevent such disorganized electric conduction and depolarization is generally known as ablation whereby local lesions of the myocardial tissue are induced in order to interrupt electric conduction of stimuli at the sites of respective lesions. To determine myocardial sites to be treated by means of ablation, monitoring of the electric potentials in a heart chamber, also referred to as mapping, is carried out.

Complex fractionated atrial electrograms (CFAE) have been identified as targets for AF ablation. Several catheter-based cardiac mapping systems have been developed that incorporate the features to map and identify areas associated with CFAE, which may function either as the drivers or the necessary substrate required for AF maintenance. However, there is no universal agreement on the precise definition of CFAE.

For example, "A New Approach for Catheter Ablation of Atrial Fibrillation: Mapping of the Electrophysiologic Substrate", a publication of the Journal of the American College of Cardiology (JACC) 2004, volume 43 pages 2044-2053, to Nademanee et al., presents CFAE-guided AF ablation in humans. According to Nademanee et al., CFAE is defined in two ways. One definition of CFAE is described as "fractionated electrograms composed of two deflections or more, and/or perturbation of the baseline with continuous deflection of a prolonged activation complex over a 10-s recording period." Another definition is described as "atrial electrograms with a very short cycle length (≤120 ms) averaged over a 10-s recording period."

"Stability of Complex Fractionated Atrial Electrograms", a publication of the Journal of Cardiovascular Electrophysiology 2012, volume 23 pages 980-987, to Lau et al., shows a systematic review of several methods to define CFAE based on time domain measurement. According to Lau et al., one method defines CFAE as the mean of time intervals between the marked deflections being less than 120 ms. Another method of Lau et al. counts ICL (Interval Confidence Level), which is the number of intervals (usually of 50-120 ms) between tagged intrinsic local activations within a sampling period, and AIPI (Average Inter-Potential Interval), which refers to the average of all intervals between 2 successive tagged deflections of >50 ms. According to Lau et al., CFAE is defined by ICL≥5 and AIPI<100 ms. A third definition of CFAE is described in Lau et al. as the presence of 2 or more successive tagged deflections with interval <50 ms and expressed as number of deflections or percentage of continuous activity. Furthermore, a fourth definition of CFAE in Lau et al. is that the electrograms show atrial complexes of >50 ms with more than 3 deviations from baseline.

Besides the time domain methods, the CFAE is also defined based on dominant frequency (DF) analysis. The principle is to transform the signal from the time domain to the frequency domain. Subsequently, the highest peak in the spectrum is generally identified as the DF. The location with the highest DF value is subject to ablation. "Complex Fractionated Atrial Electrograms: Properties of Time-Domain Versus Frequency-Domain Methods", a publication of the Heart Rhythm Journal 2009, volume 6 pages 1475-1482, to Grzeda et al., shows that the DF method appears to be more robust than the time-domain method in identifying the CFAE sites.

"Differences in Repeating Patterns of Complex Fractionated Left Atrial Electrograms in Longstanding Persistent as Compared with Paroxysmal Atrial Fibrillation", a publication of the Circulation: Arrhythmia and Electrophysiology Journal 2011, volume 4 pages 470-477, to Ciaccio et al., extends the analysis of CFAE by focusing on the spatial and temporal repeatability of CFAE patterns. Ciaccio et al. appears to combine two independent methods, linear prediction and Fourier reconstruction, to quantify the repeatability of CFAE. According to Ciaccio et al., the degree of repeatability is site-specific and different in paroxysmal compared with longstanding AF.

"Measuring the Complexity of Atrial Fibrillation Electrograms", a publication of the Journal of Cardiovascular Electrophysiology 2010, volume 21 pages 649-655, to Ng et al., evaluates Shannon's entropy (ShEn) and the Kolmogorov-Smirnov (K-S) test as statistical methods to quantify complexity of AF electrograms, and compares these measures with fractional intervals in distinguishing CFAE from non-CFAE signals. Ng et al. appears to show that ShEn could be used to automatically rank and classify CFAE electrograms, and has comparable performance to fractional intervals.

"Novel Assessment of Temporal Variation in Fractionated Electrograms Using Histogram Analysis of Local Fractionation Interval in Patients with Persistent Atrial Fibrillation", a publication of the Circulation: Arrhythmia and Electrophysiology Journal 2012, volume 5 pages 949-956, to Lin et al. applies histogram analysis for substrate mapping in patients with persistent AF. Instead of relying on the mean fractionation interval (FI), Lin et al. appears to focus on evaluating the kurtosis and skewness of the FI histogram in order to characterize the temporal variation of the FI.

World Intellectual Property Organization Patent Publication 2012/021022 entitled "Simulated Arrhythmia Catheter Ablation System", to Pak, presents a simulated arrhythmia catheter ablation system including a modeling unit, a pattern-producing unit, a mapping unit, an analysis unit, and a surgical unit. The modeling unit of Pak reproduces an atrial model by using heart image data. The pattern-producing unit produces an arrhythmia electrical-wave pattern on the atrial model. The mapping unit produces an atrial-site-specific electrical-signal map on the atrial model on which the arrhythmias electrical-wave pattern has been produced. The analysis unit discerns a core site of an electrical-wave vortex by using the atrial-site-specific electrical-signal map. The surgical unit carries out simulated catheter ablation at the core site of the electrical-wave vortex as discerned in the analysis unit.

United States Patent Publication 2007/197929 entitled "Mapping of Complex Fractionated Atrial Electrogram", to Porath et al., discloses an apparatus and a method to automatically detect and map areas of complex fractionated electrograms. According to Porath et al., electrical signal data are obtained from respective locations of a heart and automatically analyzed to identify complex fractionated electrograms. Information derived from the signal data indicative of a spatial distribution of complex fractionated electrograms in a heart is displayed. Voltage peaks having amplitudes within a predefined voltage range may be identified and peak-to-peak intervals between the identified voltage peaks that occur within a predefined time range may be identified. Location information can be obtained using a position sensor. A functional map of a heart that is coded according to average or shortest durations of the complex fractionated electrograms or according to numbers of the complex fractionated electrograms detected in respective locations can be displayed.

U.S. Pat. No. 7,904,143 entitled "Binary Logistic Mixed Model for Complex Fractionated Atrial Electrogram Procedures", to Ishay et al., shows methods and a medical apparatus for identifying CFAE locations. The method of Ishay et al. appears to locate an arrhythmogenic focus in a heart of a living subject by obtaining training electrical signal data from respective training locations of a training set of hearts, which are automatically analyzed to identify training complex fractionated electrograms (CFAEs) therein. A plurality of observers determines the medical significance of the CFAEs, which is recorded and a first estimation is generated at the respective training locations by fitting a mixed regression model to the training CFAEs and the determinations of medical significance. In a next step, patient electrical signal data from respective locations of a patient heart are obtained and automatically analyzed to identify CFAEs. The mixed regression model is applied on the CFAEs to obtain second estimations of medical significance and an indication that one or more of the respective locations of the patient heart are medically significant are displayed.

U.S. Pat. No. 8,315,696 entitled "Identifying Critical CFAE Sites Using Contact Measurement", to Schwartz, shows a method and a mapping apparatus for mapping complex fractionated electrograms by a probe at respective locations in a chamber of a heart of a subject. The mapping apparatus of Schwartz includes a probe and a processor. The probe is configured to sense electrical activity in a chamber of a heart of a subject. The processor is configured to receive and process electrical inputs from the probe at multiple locations in the chamber. The processor identifies complex fractionated electrograms and measures at each location a respective contact quality between the probe and tissue in the chamber. The processor creates a map of the CFAE in the chamber using the electrical inputs and measured contact quality to distinguish between active and passive CFAEs. The apparatus may include an energy generator for ablation of sites at which CFAE were detected while contact quality satisfied a predetermined contact criterion.

Generally, it is likely that CFAE defined by different algorithms may represent different aspects of the underlying pathophysiology of atrial fibrillation (AF). For example, generally, it has been shown that there is poor anatomic overlap between CFAE defined by multi-component/continuous electrograms (EGMs) and CFAE defined by AF cycle length <120 ms, as disclosed by Lee et al. in "Relationship Among Complex Signals, Short Cycle Length Activity, and Dominant Frequency in Patients with Long-Lasting Persistent AF" published in the Heart Rhythm Journal 2011, volume 8 pages 1714-1719. Generally, most methods, including time domain methods and dominant frequency methods, characterize CFAE based on the fractionation intervals, ignoring information related to the amplitude variation of the electrograms. Other features of the electrogram morphology that reflect fractionated signal complex, such as the number of local peaks in a complex, the number of zero-crossings in a complex, the frequency content of a complex, or the like are generally also ignored.

Although the amplitude information is taken into consideration when quantifying the atrial electrogram complexity, as discussed in Ng et al. and Ciaccio et al., every data sample of the electrograms, including those in the signal baseline is included in the calculation, thus rendering these methods subject to the influence of recording noise, as well as the far-field components generated from distant atrial sites. Moreover, the clinical utility of these methods has not been confirmed.

As such, in view of the above, there is a need for a device for monitoring and evaluating electrogram signals representing electric activities of a heart chamber.

BRIEF SUMMARY OF THE INVENTION

One or more embodiments of the invention include a device that monitors and evaluates electrogram signals representing electric activities of a heart chamber. In at least one embodiment, the device includes a signal input that may be connected to a mapping catheter and a signal processing and evaluation unit to process and evaluate electrogram signals received by the signal input. In one or more embodiments, the mapping catheter includes at least one electrode pole that picks up electric potentials and generates electrogram signals from the picked up electric potentials. The signal processing and evaluation unit, in at least one embodiment, may perform a number of steps when an electrogram signal is received by the signal input. By way of one or more embodiments, the steps include one or more of identifying waveform deflections in the electrogram signal, measuring deflection intervals between each pair of consecutive deflection complexes in the electrogram signal, measuring at least one metric that includes a morphology of a deflection complex in the electrogram signal, generating a multi-dimensional deflection vector of at least two dimensions for each identified deflection, with at least one element being the deflection interval, determining a distance between each pair of consecutive deflections from the multi-dimensional deflection vectors, and determining a cumulative distance between deflections in a time window of predetermined length.

According to at least one embodiment of the invention, the distance may, for example, be a weighted city block distance, a weighted Euclidean distance, or the like, wherein the distance between each pair of consecutive deflections is a distance between two multi-dimensional deflection vectors associated with two consecutive deflections. In one or more embodiments, the degree of complex fractionated atrial electrogram (CFAE) for a segment of an atrial electrogram (EGM) signal is calculated based on the cumulative distance between deflections within the segment.

One or more embodiments of the invention provide a novel apparatus to quantify the degree of CFAE based on multi-dimensional assessment of the regularity of the EGM deflections, which yields an improved measure for detection of CFAE. At least one embodiment of the invention is advantageous in that it comprises not only temporal domain analysis of the fractionation intervals, but also an analysis of the fractionated wave amplitude and/or other metrics that characterize the fractionated morphology of the deflection complexes in the electrogram signals. According to one or more embodiments, the degree of CFAE at each site may be measured in real time through a novel distance measure, which assesses the regularity of deflection waves in a multi-dimensional space. By mapping the degree of CFAE, in at least one embodiment, targeted atrial fibrillation ablation may be applied for more effective therapy.

In at least one embodiment of the invention, the device may convert quasi non-discrete sampled values of preselected dimensions of the multi-dimensional deflection vector to discrete values. The quasi non-discrete sampled values, in one or more embodiments, are the sample values obtained from a measurement device, e.g., the mapping catheter. In at least one embodiment, the discrete values may have a much lower resolution than the quasi non-discrete sampled values and may, for example, be obtained by coarse-graining of the quasi non-discrete sampled values or the like. In one or more embodiments, the device may determine a distance between each pair of consecutive deflections based on the converted discrete values of the multi-dimensional deflection vector. In at least one embodiment of the invention, the signal processing and evaluation unit may limit the converted discrete values of the multi-dimensional deflection vector to a predefined range with predetermined upper and lower interval thresholds. In at least one embodiment, the signal processing and evaluation unit may bin converted discrete values according to a predefined bin width. For example, in one or more embodiments, the deflection interval may be limited to a range between 20 ms and 140 ms, and a bin width may be set to 10 ms resulting in 14 bins. In at least one embodiment of the invention, similar limiting and coarse-graining operations may be performed for quasi non-discrete parameters, such as for example metrics extracted from a frequency domain or a complexity measure.

By way of at least one embodiment, the signal processing and evaluation unit may process position signals, which represent electrode poles location coordinates. In one or more embodiments, the signal processing and evaluation unit may also process electrogram signals and position signals. In at least one embodiment, each position signal may be associated to at least one corresponding electrogram signal of the corresponding electrode pole. In at least one embodiment of the invention, the signal processing and evaluation unit may associate a location coordinate represented by the position signal to the determined distance between each pair of consecutive deflections. In one or more embodiments, the signal processing and evaluation unit may include a module that may perform the processing and evaluation of the position signals.

According to at least one embodiment of the invention, the device may be connected to or include a display unit. In one or more embodiments, the display unit may display a distribution of determined cumulative distances between deflections at different electrode pole locations in a reconstructed anatomical model of a heart chamber. In at least one embodiment, the display unit may display scatter plots of deflection vectors associated with a plural of deflection complexes within a time window of an electrogram signal. In one or more embodiments, the display unit may display other data received from the device.

In at least one embodiment of the invention, the device may include or may be connected to an ablation unit. The ablation unit, in one or more embodiments, may target the electrode poles location coordinates or probing sites with the highest determined cumulative distance between deflections for ablation. In at least one embodiment, the ablation unit may target sites in dependence of other parameters.

In at least one embodiment, the signal processing and evaluation unit may perform the identification of waveform deflections through an adaptive threshold method. In one or more embodiments, a deflection complex is detected in the adaptive threshold method when the amplitude of the electrogram signal crosses a threshold value, which is adaptive to a previously detected deflection peak amplitude.

By way of at least one embodiment, one metric of the at least one metric that characterizes the morphology of a deflection complex in the electrogram signal measured by the signal processing and evaluation unit is a peak-to-peak amplitude. In one or more embodiments, the at least one metric may include the number of zero crossings within the deflection complex, the number of local peaks in the deflection complex, where a local peak is found if the slope of the signal changes from positive to negative, or from negative to positive, the absolute area under the deflection complex, the width of the deflection complex, the ratio of the positive peak amplitude to the negative peak amplitude of the deflection complex, or the like. In at least one embodiment, the morphology of the deflection complex may be characterized by a metric extracted by a basis of a vector space, such as from one or more of the frequency domain, leading to metrics such as a dominant frequency, a bandwidth of the frequency spectrum, and a ratio between dominant frequency to the bandwidth of the frequency spectrum, or the like. In one or more embodiments, the morphology of the deflection complex may be characterized by metrics that measure the complexity of the deflection complex, such as Shannon's entropy, approximate entropy, or the like. In at least one embodiment, each deflection complex may be associated with one or more measured metrics that characterize the morphological feature of the deflection complex.

According to at least one embodiment of the invention, the distance between each pair of consecutive deflections may be calculated using a weighted city block distance. In one or more embodiments, the weighted city block distance between A and B may be defined as:

$$D(A, B) = \sum_{i=1}^{n} |a(i) - b(i)| \times w(i)$$

where $||$ is the absolute operator, $A=[a(1), a(2), \ldots a(n)]$ and $B=[b(1), b(2), \ldots b(n)]$ are two n-dimensional deflection vectors associated with two consecutive deflections, where a(i) and b(i) represent the respective coordinate values along the i-th dimension (for i=1 . . . n), which may be discrete or quasi non-discrete, and w(i) is a predefined weight factor associated with the i-th dimension. In at least one embodiment, the weight factors may include positive integers. In one or more embodiments, the coordinate values along the i-th dimension may be discrete. In at least one embodiment of the invention, the distance between each pair of consecutive deflections may be calculated by another distance measure, for example weighted Euclidean distance or the like.

By way of one or more embodiments, the window length of an electrogram signal segment may be predefined or user programmable. In at least one embodiment, the window length may be larger than 1 s, for example between 3 s and 10 s. In at least one embodiment, the signal processing and evaluation unit may continually evaluate electrogram signals received by the signal input over a moving window of the electrogram signal, such that the degree of CFAE in the respective channel may be measured and displayed in real time.

In one or more embodiments, the device may determine sites in a heart chamber that show complex fractionated atrial electrograms. In at least one embodiment, the device may be connected to or includes an ablation unit, wherein the ablation unit ablates sites in a heart chamber that show complex fractionated atrial electrograms.

In at least one embodiment, the signal processing and evaluation unit may include one or more of a deflection detection unit, a parameter measurement unit, and a parameter evaluation unit. In one or more embodiments, the deflection detection unit may identify waveform deflections in the electrogram signal. In at least one embodiment, the parameter measurement unit may measure deflection intervals between each pair of consecutive deflection complexes in the electrogram signal and measure at least one metric that characterizes the morphology of a deflection complex in the electrogram signal. By way of at least one embodiment, the parameter evaluation unit may perform one or more tasks or steps including generating a multi-dimensional deflection vector of at least two dimensions for each identified deflection, wherein at least one element is the deflection interval, limiting and coarse-graining preselected dimensions of coordinate values, determining a distance between each pair of consecutive deflections from the multi-dimensional deflection vectors, and determining a cumulative distance between deflections in a time window of predetermined length. In one or more embodiments, the signal processing and evaluation unit may include a module for each task or step performed by the deflection detection unit, the parameter measurement unit, and the parameter evaluation unit of the signal processing and evaluation unit. In at least one embodiment, one or more of the steps may be performed by an alternative module or modules of the signal processing and evaluation unit.

One or more embodiments of the invention include a method of operating a device for monitoring electrical activities in a heart chamber including one or more of receiving an electrogram signal, identifying waveform deflections in the electrogram signal, measuring deflection intervals between each pair of consecutive deflection complexes in the electrogram signal, measuring at least one metric that characterizes the morphology of a deflection complex in the electrogram signal, generating a multi-dimensional deflection vector of at least two dimensions for each identified deflection, wherein at least one element is the deflection interval, limiting and coarse-graining preselected dimensions of coordinate values, determining a distance between each pair of consecutive deflections from the multi-dimensional deflection vectors, and determining a cumulative distance between deflections in a time window of predetermined length. In at least one embodiment, the step of limiting and coarse-graining preselected dimensions of coordinate values may be omitted.

One or more embodiments of the method may include receiving a position signal. In at least one embodiment, the position signal represents an electrode pole location. In at least one embodiment, the method may include a step of associating the electrode pole location represented by the position signal to an electrogram signal. In one or more embodiments, the method may include a step of associating the electrode pole location represented by the position signal to the determined distance between each pair of consecutive deflections or the cumulative distance.

At least one embodiment of the invention includes a method for a mapping catheter which probes different sites of a heart chamber to obtain each site's location coordinate, and quantify the degree of CFAE at each probed atrial site. In one or more embodiments, a map of the CFAE in the atrial chamber may be created and the sites with the highest degree of CFAE are targeted for ablation. In at least one embodiment, the method to quantify the degree of CFAE may be based on temporal domain analysis of the fractionation intervals, and the analysis of the fractionated wave amplitude and/or other metrics that characterize the fractionated morphology of the deflection complexes in the electrogram signals. In one or more embodiments, scatter plots may be created to visualize the temporal-amplitude distribution of the fractionated waves, and distance measures may be calculated to quantify the degree of CFAE. In at least one embodiment, metrics of the fractionated electrogram may be measured and incorporated to quantify the CFAE in a multi-dimensional space. By way of one or more embodiments, the CFAE is quantified based on at least two independent dimensions of an atrial electrogram signal.

BRIEF DESCRIPTION OF THE DRAWINGS

The above and other aspects, features and advantages of at least one embodiment of the invention will be more apparent from the following more particular description thereof, presented in conjunction with the following drawings wherein.

DETAILED DESCRIPTION OF THE INVENTION

The following description is of the best mode presently contemplated for carrying out at least one embodiment of the invention. This description is not to be taken in a limiting sense, but is made merely for the purpose of describing the general principles of the invention. The scope of the invention should be determined with reference to the claims.

Figure 1:
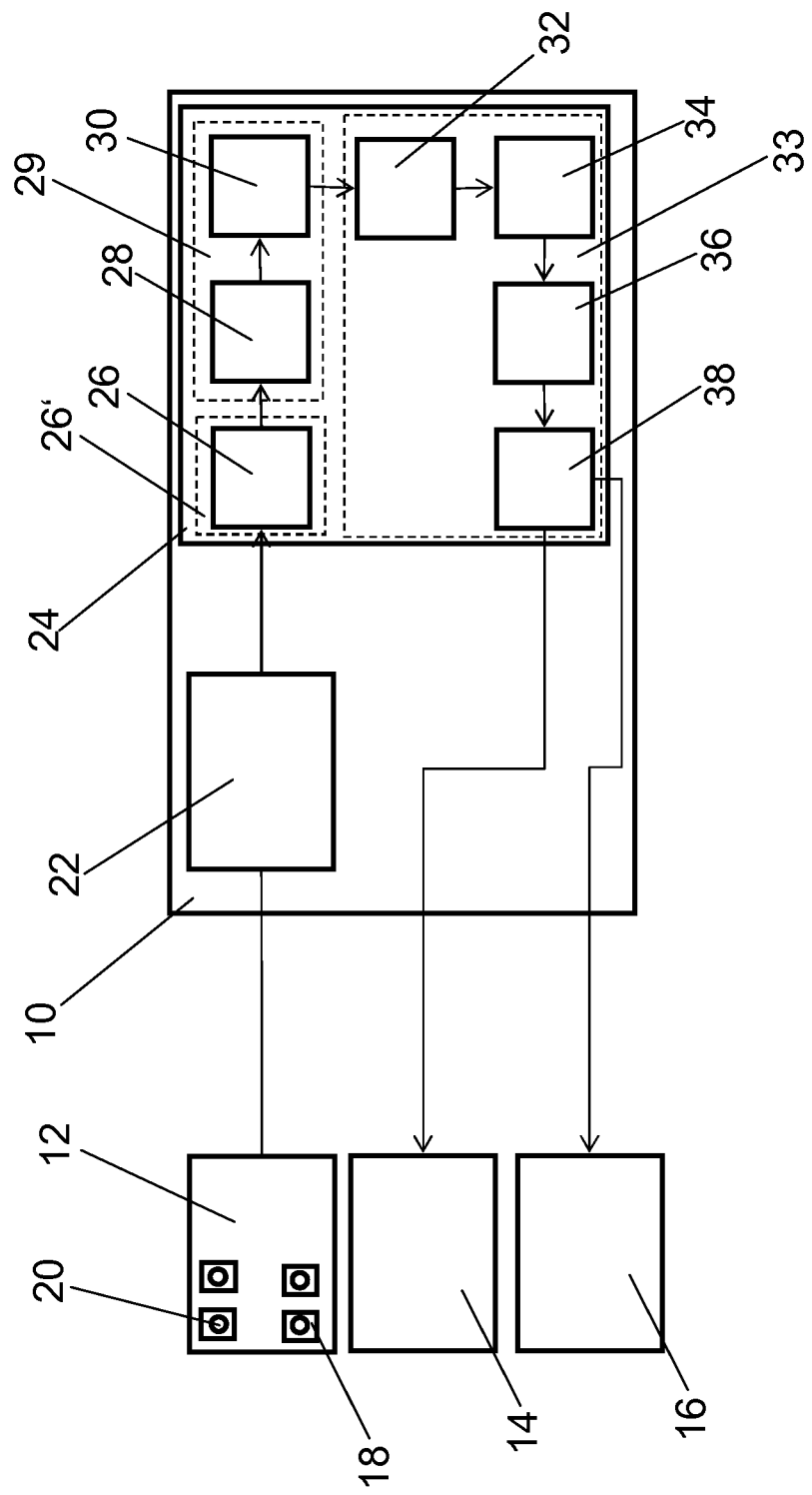
FIG. 1 is a schematic block diagram of a device according to at least one embodiment of the invention.

FIG. 1 shows a block diagram of a device 10, which is operatively connected to a mapping catheter 12, a display unit 14 and an ablation unit 16, according to at least one embodiment of the invention. The mapping catheter 12, in one or more embodiments, includes a plurality of electrode poles 18 which may sense electrical activities at different sites of a heart chamber. In at least one embodiment of the invention, the mapping catheter 12 includes position sensors 20 that may obtain each probing site's and electrode poles location coordinate. In one or more embodiments, electrogram signals and position signals acquired by the mapping catheter 12 are transmitted to a signal input 22 of the device 10. In at least one embodiment, the signals received by the signal input 22 are processed in a signal processing and evaluation unit 24. By way of at least one embodiment, the signal processing and evaluation unit 24 includes modules 26, 28, 30, 32, 34, 36 and 38, which may be grouped in or included in a deflection detection unit 26' that detects waveform deflections in the electrogram signal, a parameter measurement unit 29 that measures parameters in the electrogram signal, and a parameter evaluation unit 33 that evaluates the parameters measured in the parameter measurement unit 29.

In one or more embodiments, waveform deflection identification module 26 may identify waveform deflections in electrogram signals. In at least one embodiment, the deflection detection unit 26' may perform the tasks of the identification module 26.

By way of one or more embodiments, deflection interval measurement module 28 may measure deflection intervals between each pair of consecutive deflection complexes in the electrogram signal. In at least one embodiment, metric measurement module 30 may measure metrics that characterize morphologies of deflection complexes in the electrogram signal. In one or more embodiments, the parameter measurement unit 29 may perform the tasks of the interval measurement module 28 and the metric measurement module 30.

According to at least one embodiment of the invention, deflection vector generation module 32 may generate multi-dimensional deflection vectors of at least two dimensions for each identified deflection, wherein at least one element is the deflection interval. In one or more embodiments, coarse-graining module 34 may limit and coarse-grain preselected dimensions of coordinate values, e.g. by forming discrete values from respective sampled and thus quasi non-discrete measured values. In at least one embodiment, distance determination module 36 may determine a distance between the multi-dimensional deflection vectors that represent each pair of consecutive deflections. In one or more embodiments, cumulative distance determination module 38 may determine a cumulative distance between deflections in a time window of predetermined length. The parameter evaluation unit 33, in at least one embodiment, may perform some or all of the tasks of modules 32, 34, 36 and 38.

A detailed description of the performed tasks of the modules 26, 28, 30, 32, 34, 36 and 38 of the signal processing and evaluation unit 24 is presented in the description of FIG. 2 below, according to one or more embodiments of the invention.

By way of at least one embodiment, the cumulative distance determined in module 38 may be used to quantify the complex fractionated atrial electrogram (CFAE) on different probing sites. In one or more embodiments, the CFAE data may be transmitted to the display unit 14, which may display the distribution of calculated CFAE at different atrial sites in a reconstructed anatomical model of the atrial chamber. In at least one embodiment, the CFAE data may be transmitted to the ablation unit 16, which may target the sites or electrode pole locations with the highest degree of CFAE, respectively cumulative distance between deflections, for ablation.

According to one or more embodiments of the invention, the device 10 may include the mapping catheter 12, the display unit 14 and/or the ablation unit 16. In at least one embodiment, the mapping catheter 12 may include only one electrode pole 18 and one or more position sensors 20. If the mapping catheter 12 is equipped with only one electrode pole 18, in at least one embodiment, the mapping may be performed by variation of the position of the mapping catheter 12. In one or more embodiments, the position signal may be processed and evaluated in the signal processing and evaluation unit 24 or in a module of the signal processing and evaluation unit 24. In at least one embodiment, the signal processing and evaluation unit 24 may associate each position signal to at least one corresponding electrogram signal and/or may associate a location coordinate represented by the position signal to the determined distance between each pair of consecutive deflections.

In one or more embodiments, the method to quantify the degree of CFAE is based on multi-dimensional analysis of the atrial electrogram. The details of the method to quantify the degree of CFAE, respectively the details to determine the cumulative distance, according to at least one embodiment of the invention, are described below.

Figure 2:
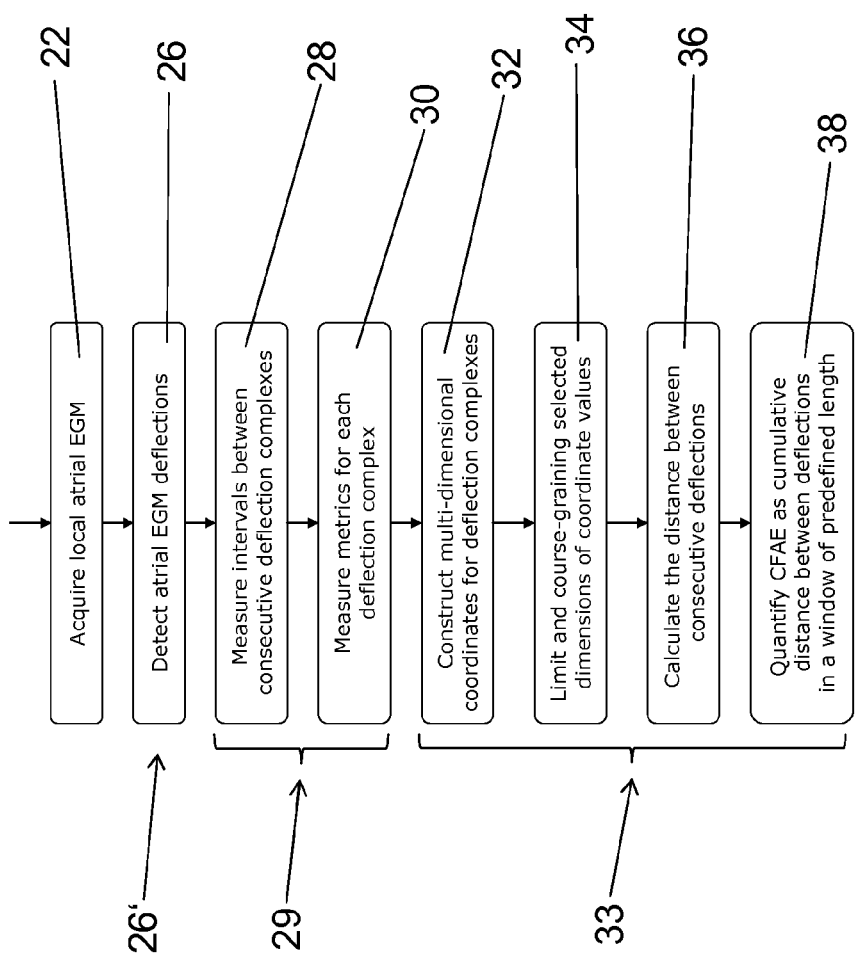
FIG. 2 is a flow chart illustrating the operation of the device of FIG. 1, according to at least one embodiment of the invention.

FIG. 2 is a flowchart that shows the steps of quantifying CFAE with the device 10 and components/modules of device 10 in which the steps are performed, according to at least one embodiment of the invention. As shown in FIG. 1, in at least one embodiment, first the system acquires the local atrial electrogram (EGM) from the electrodes poles 18 that are close to the probing site, which include the EGM in an electrogram signal and transmit it to the signal input 22 of the device 10. In one or more embodiments, the waveform deflections in the acquired atrial electrogram signal are then identified in module 26, for example by a peak detection algorithm, such as through a depolarization detection algorithm. In at least one embodiment, the depolarization detection algorithm may be implemented through an adaptive threshold method, in which a deflection complex is detected when the EGM amplitude crosses a threshold value, which is adaptive to the previously detected deflection peak amplitude. In one or more embodiments, after the detection of an atrial depolarization complex, a predefined refractory window may be applied to prevent the algorithm from detecting another threshold crossing that is too close to the previously detected deflection complex.

In at least one embodiment, after the EGM deflections are detected through a peak detection algorithm, the deflection intervals between each pair of consecutive deflection complexes are measured in module 28. In one or more embodiments, each deflection is associated with one deflection interval. In at least one embodiment, the deflection interval associated with a deflection complex may be the interval immediately preceding the deflection complex or the interval immediately after the deflection complex.

By way of one or more embodiments, the metrics that characterize the morphology of the deflection complex are then measured in module 30. In at least one embodiment, one exemplary metric is the peak-to-peak amplitude of the deflection complex. Another exemplary metric, in at least one embodiment, is the number of zero crossings within the deflection complex. Yet another metric, in at least one embodiment, is the number of local peaks in the deflection complex, where a local peak is found if the slope of the signal changes from positive to negative, or from negative to positive. According to one or more embodiments of the invention, other metrics that characterize the shape of the deflection complex include, but are not limited to, the absolute area under the deflection complex, the width of the deflection complex, the ratio of the positive peak amplitude to the negative peak amplitude of the deflection complex, or the like. In at least one embodiment, the morphology of the deflection complex may be characterized by the metrics extracted by a basis, such as from the frequency domain. For example, in one or more embodiments, a frequency spectrum of the deflection complex may be calculated, from which metrics such as a dominant frequency, a bandwidth of the spectrum, and a ratio between dominant frequency to a bandwidth of the spectrum, or the like may be obtained. In at least one embodiment, the morphology of the deflection complex may be characterized by metrics that measure the complexity of the deflection complex, such as Shannon's entropy, approximate entropy, or the like. Therefore, in one or more embodiments, each deflection complex is associated with one or more measured metrics that characterize the morphological feature of the deflection complex.

Then, in at least one embodiment of the invention, for each identified EGM deflection, a multi-dimensional deflection vector is generated in module 32. In one or more embodiments, at least one element of the deflection vector is the deflection interval associated with a deflection complex. According to at least one embodiment, other elements of the deflection vector include the measured metrics that characterize the morphology of the deflection complex as described above. For example, in one or more embodiments of the invention, the deflection complex k may be associated with a constructed two-dimensional deflection vector ($L_k$, $A_k$), where $L_k$ is the deflection interval associated with the deflection complex k, and $A_k$ is peak-peak amplitude of the deflection complex k. In another example, the deflection complex k can be associated with a constructed three-dimensional deflection vector ($L_k$, $A_k$, $X_k$) where $L_k$ is the deflection interval associated with the deflection complex k, $A_k$ is peak-peak amplitude of the deflection complex k, and $X_k$ is number of zero-crossings within the deflection complex k. In one or more embodiments, the deflection complex k may be associated with a constructed four-dimensional deflection vector ($L_k$, $A_k$, $X_k$, $P_k$) where $L_k$ is the deflection interval associated with the deflection complex k, $A_k$ is peak-peak amplitude of the deflection complex k, $X_k$ is number of zero-crossings within the deflection complex k, and $P_k$ is number of local peaks within the deflection complex k. In at least one embodiment, the dimension of the deflection vector may vary depending on the number of metrics measured from the deflection complexes, but is always greater than 1.

Next, by way of one or more embodiments, preselected dimensions of coordinate that are quasi non-discrete sampled values are converted to discrete values through limiting and coarse-graining operations in module 34. In at least one embodiment, the deflection intervals are limited to a predefined range with predetermined upper and lower interval thresholds, and are binned according to predefined bin width. For example, in one or more embodiments, the deflection interval may be limited to the range between 20-140 ms, and the bin width may be set to 10 ms. Then, in at least one embodiment, each deflection interval (DI) may be assigned to one of the following 14 discrete bins: DI<20 ms, 20≤DI<30 ms, 30≤DI<40 ms, . . . , 130≤DI<140 ms, DI>140 ms. Accordingly, in one or more embodiments, the deflection interval may be replaced with the corresponding bin index ranging from 1 to 14. Similarly, in at least one embodiment of the invention, if peak-peak amplitude (PA) is one dimension of the coordinate, then the amplitude value may be limited to a range, e.g., 0.1-1.0 mV. In one or more embodiments, if the bin width is set to 0.1 mV, then the peak-peak amplitude may be binned to one of 11 discrete bins: PA<0.1 mV, 0.1≤PA<0.2 mV, 0.2≤PA<0.3 mV, . . . , 0.9≤PA<1.0 mV, PA>1.0 mV. Accordingly, in at least one embodiment, the peak-peak amplitude may be replaced with the corresponding bin index ranging from 1 to 11. According to one or more embodiments, other limit values (such as those based on error minimization) and bin widths (whose edges are based on a log scale for example) may be similarly applied. In at least one embodiment, for other quasi non-discrete parameters, such as the metrics extracted from the frequency domain or the complexity measures, similar limiting and coarse-graining operations may be performed.

Then, in one or more embodiments, the distance between each pair of consecutive deflections is determined in module 36. By way of at least one embodiment, the distance between each pair of consecutive deflections is calculated using a weighted city block distance. Denote A=[a(1), a(2), . . . a(n)] and B=[b(1), b(2), . . . b(n)] are two n-dimensional deflection vectors associated with two consecutive deflections, where a(i) and b(i) represent the respective discrete coordinate values along the i-th dimension (for i=1 . . . n), according to at least one embodiment of the invention. In one or more embodiments, the weighted city block distance between A and B is defined as:

$$D(A, B) = \sum_{i=1}^{n} |a(i) - b(i)| \times w(i)$$

where || is the absolute operator, and w(i) is a predefined weight factor associated with the i-th dimension. In at least one embodiment, the weight factors may be positive integers. In one or more embodiments, if all weight factors are set to 1, then the coordinate differences in all dimensions are treated equally. On the other hand, in at least one embodiment, if the weight factors are set to different values, then they apply different weights to different dimensional measures. For example, in one or more embodiments, if the weight factor for the deflection interval is set to 2, whereas the weight factor for the peak-peak amplitude is set to 1, then the impact of difference in deflection interval is twice as that of difference in peak-peak amplitude. Although weighted city block distance is used in this example, in at least one embodiment of the invention, it should be understood that other distance measures, such as weighted Euclidean distance, may be used. In one or more embodiments, discrete values are used in calculating the distance. Thus, in at least one embodiment, the difference between two deflection intervals is not measured in milliseconds. Instead, in one or more embodiments, the module 36 measures the difference between the corresponding bin indexes, thus the distance has no unit. Similarly, in at least one embodiment, the difference between two peak-peak amplitude values is not measured in millivolt. Instead, in one or more embodiments, the module 36 measures the difference between the corresponding bin indexes, thus the difference between two peak-peak amplitude values has no unit.

According to at least one embodiment of the invention, the CFAE for a segment of atrial EGM is determined based on the cumulative distance between deflections within the segment in module 38. In one or more embodiments, the window length of the EGM segment is predefined or user programmable, for example larger than 1 s, such as in a range between 3 s and 10 s. At least one embodiment, the CFAE is continually evaluated over a moving window of the atrial EGM, such that the degree of CFAE in that channel may be measured and displayed in real time.

FIGS. 3 to 6 illustrate examples of scatter plots of deflection vectors on a 2D coordinate system, where one dimension is the deflection interval 40, and another dimension is the peak-peak deflection amplitude 42, according to at least one embodiment of the invention. In one or more embodiments, the 2D plot is divided into grids of predefined resolution in both axes (deflection interval resolution: 10 ms, peak-peak amplitude resolution: 0.1 mV), with square bins 44 having a size of 10 ms times 0.1 mV.

Figure 3:
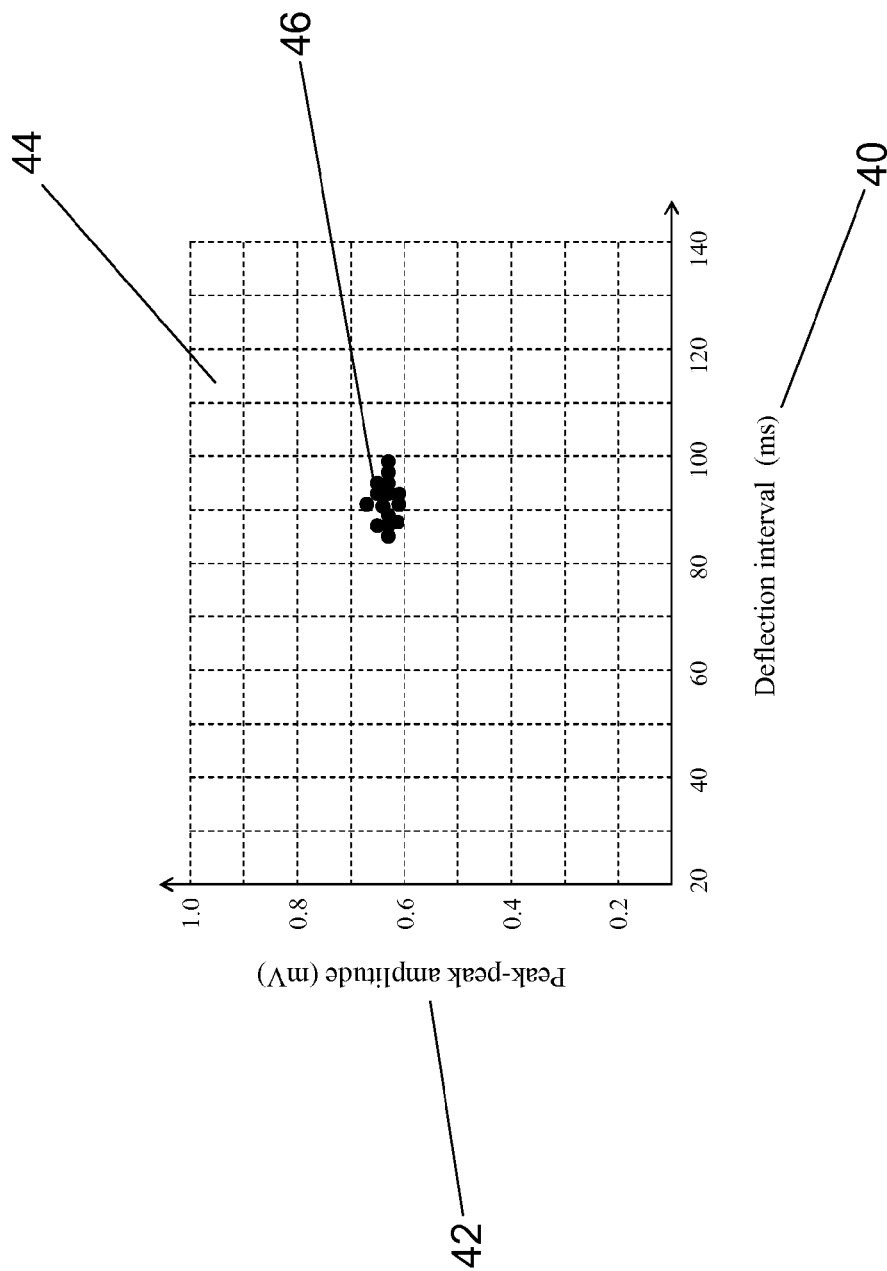
FIG. 3 is a first example of a scatter plot of deflection vectors, which shows a CFAE corresponding to a non-fractionated atrial EGM.

FIG. 3 illustrates a first example of a scatter plot of the deflection vectors 46 associated with a plural of deflection complexes within a window of atrial EGM that has regular deflection intervals 40 and stable peak-peak amplitude 42, according to at least one embodiment of the invention. In one or more embodiments, the deflection vectors 46 are concentrated in a condensed area within 2 square bins 44. In at least one embodiment, the distance between each pair of consecutive deflections is small, limited to about 1 bin in either horizontal or vertical axis. Consequently, in one or more embodiments, the CFAE, or the cumulative distance between deflections is small, indicating the corresponding atrial EGM is not fractionated.

Figure 4:
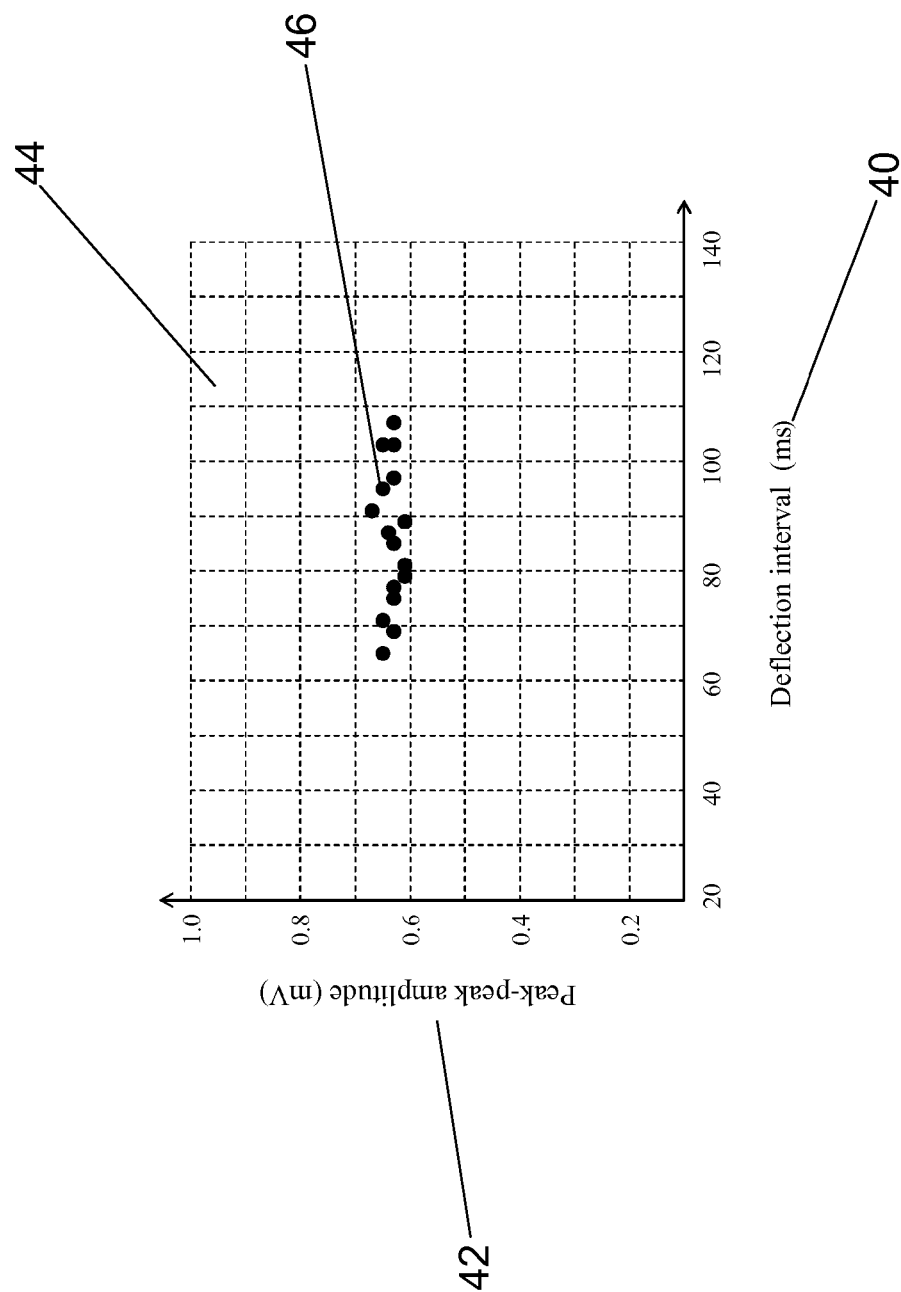
FIG. 4 is a second example of a scatter plot of deflection vectors, which shows a CFAE corresponding to a partially fractionated atrial EGM.

FIG. 4 illustrates a second example of a scatter plot of the deflection vectors 46 associated with a plural of deflection complexes within a window of atrial EGM that includes irregular deflection intervals 40 but regular peak-peak amplitude 42, according to at least one embodiment of the invention. In one or more embodiments, the deflection vectors 46 are concentrated in a narrow row within 1 square bin 44 but widely spread in multiple columns within 5 square bins 44, covering a total scatter area of 5 square bins 44. In at least one embodiment, the distance between each pair of consecutive deflections is moderate, limited along vertical axis but large along horizontal axis. Consequently, in one or more embodiments, the CFAE, or the cumulative distance between deflections is moderate, indicating the corresponding atrial EGM is partially fractionated.

Figure 5:
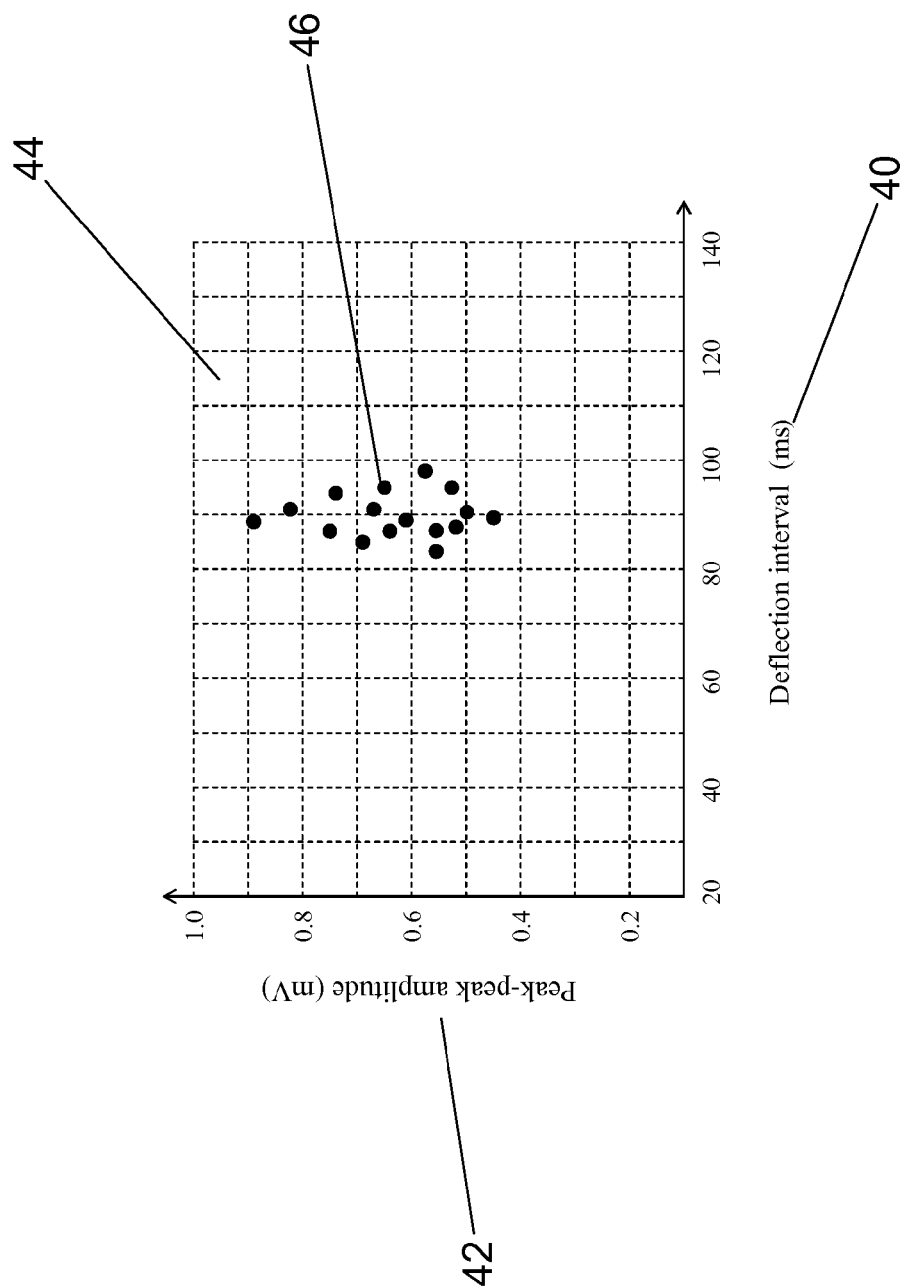
FIG. 5 is a third example of a scatter plot of deflection vectors, which shows a CFAE corresponding to a partially fractionated atrial EGM.

FIG. 5 illustrates a third example of a scatter plot of the deflection vectors 46 associated with a plural of deflection complexes within a window of atrial EGM that includes regular deflection intervals 40 but irregular peak-peak amplitude 42, according to at least one embodiment of the invention. In one or more embodiments, the deflection vectors 46 are concentrated column-wise within 2 square bins 44 but widely spread in multiple rows within 5 square bins 44 and cover a total scatter area of 10 square bins 44. In at least one embodiment, the distance between each pair of consecutive deflections is moderate, limited in horizontal axis but large in vertical axis. Consequently, in one or more embodiments, the CFAE, or the cumulative distance between deflections is moderate, indicating the corresponding atrial EGM is partially fractionated.

Figure 6:
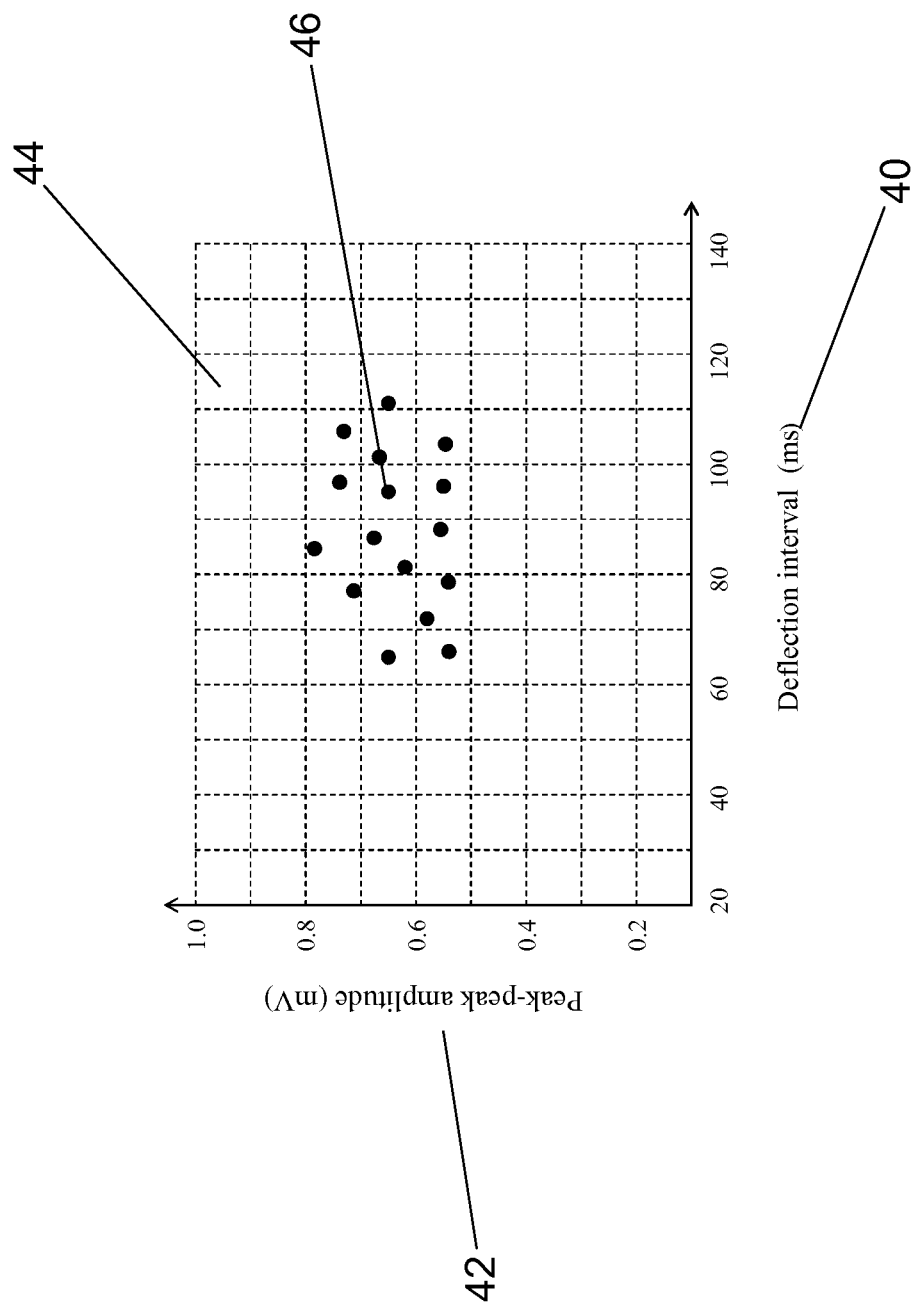
FIG. 6 is a fourth example of a scatter plot of deflection vectors, which shows a CFAE corresponding to a highly fractionated atrial EGM.

FIG. 6 illustrates fourth example of a scatter plot of the deflection vectors 46 associated with a plural of deflection complexes within a window of atrial EGM that includes both irregular deflection intervals 40 and irregular peak-peak amplitude 42, according to at least one embodiment of the invention. In one or more embodiments, the deflection vectors 46 are sparsely scattered in the plot, wherein they are widely spread column-wise within 4 to 6 square bins 44 and also widely spread in multiple rows within 3 square bins 44, and cover a total scatter area of 14 square bins 44. In one or more embodiments, the distance between each pair of consecutive deflections is large in both horizontal axis and vertical axis. Consequently, in at least one embodiment, the CFAE, or the cumulative distance between deflections is large, indicating the corresponding atrial EGM is highly fractionated.

By way of one or more embodiments, the scatter plots may be used to visualize the temporal-amplitude distribution of the fractionated waves. In at least one embodiment, the trajectories (i.e. the lines between each pair of adjacent deflection vectors) may be plotted to reveal the transition from one deflection vector to another, and the distances between pairs of deflection vectors. It should be understood that, in one or more embodiments, other dimensions of the coordinates may be used to construct the scatter plots to reveal the degree of fractionation, within the scope of the invention. It should also be understood that, in one or more embodiments, other methods to characterize the spatial distribution of the scatter plot, such as the eccentricity of the best fit ellipse surrounding the samples, the slope of the best fit linear regression line, the non-empty cells/rows/columns, or the like, may be used within the scope of invention.

Although an exemplary embodiment of the invention has been shown and described, it should be apparent to those of ordinary skill that a number of changes and modifications to the invention may be made without departing from the spirit and scope of the invention. All such changes, modifications and alterations should therefore be recognized as falling within the scope of the present invention.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

What is claimed is:

1. A device for monitoring and evaluating electrogram signals representing electric activities of a heart chamber, said device comprising:
    a signal input connected to a mapping catheter, wherein the mapping catheter comprises at least one electrode pole that picks up electric potentials and generates electrogram signals from the picked up electric potentials, wherein said signal input receives the electrogram signals, and
    a signal processing and evaluation unit that processes and evaluates the electrogram signals received at the signal input;
    wherein when an electrogram signal is received by the signal input, the signal processing and evaluation unit identifies waveform deflections in the electrogram signal,
    measures deflection intervals between each pair of consecutive deflection complexes in the electrogram signal, measures at least one metric that characterizes a morphology of a deflection complex in the electrogram signal, generates a multi-dimensional deflection vector of at least two dimensions for each identified deflection using said at least one metric, wherein at least one element is the deflection interval, determines a distance between each pair of consecutive deflections from the multi-dimensional deflection vectors, and determines a cumulative distance between deflections in a time window of predetermined length;

wherein the device is connected to an ablation unit, wherein the ablation unit targets the electrode pole location with a highest determined cumulative distance from said determined cumulative distance between deflections to ablate the heart chamber, and, wherein said device determines sites in the heart chamber that show complex fractionated atrial electrograms and wherein said ablation unit is configured to ablate the sites in the heart chamber that show complex fractioned atrial electrograms based on said highest determined cumulative distance.

2. The device according to claim 1, wherein the signal processing and evaluation unit converts quasi non-discrete sampled values of preselected dimensions of the multi-dimensional deflection vector to discrete values, and determines a distance between each pair of consecutive deflections based on the converted discrete values of the multi-dimensional deflection vector.

3. The device according to claim 2, wherein the signal processing and evaluation unit limits the converted discrete values of the multi-dimensional deflection vector to a predefined range with predetermined upper and lower interval thresholds, and bins the converted discrete values according to predefined bin width.

4. The device according to claim 1, wherein the signal processing and evaluation unit processes electrogram signals in combination with position signals, wherein the position signals represent electrode poles location coordinates, and wherein each position signal is associated to at least one corresponding electrogram signal of the corresponding electrode pole.

5. The device according to claim 4, wherein the signal processing and evaluation unit associates a location coordinate represented by the position signal to the determined distance between each pair of consecutive deflections.

6. The device according to claim 1, wherein the device is connected to a display unit, wherein the display unit displays a distribution of said determined cumulative distances between deflections at different electrode pole locations in a reconstructed anatomical model of a heart chamber.

7. The device according to claim 1, wherein the signal processing and evaluation unit performs the identification of waveform deflections through an adaptive threshold method, in which a deflection complex is detected when an amplitude of the electrogram signal crosses a threshold value which is adaptive to a previously detected deflection peak amplitude.

8. The device according to claim 1, wherein said at least one metric that characterizes a morphology of a deflection complex in the electrogram signal measured by the signal processing and evaluation unit comprises a peak-to-peak amplitude.

9. The device according to claim 1, wherein the signal processing and evaluation unit determines the distance between each pair of consecutive deflections using a weighted city block distance.

10. The device according to claim 1, wherein the signal processing and evaluation unit continually evaluates electrogram signals received by the signal input.

11. The device according to claim 1, wherein said at least one metric that characterizes a morphology of a deflection complex in the electrogram signal measured by the signal processing and evaluation unit comprises a metric extracted by a basis of a vector space.

12. The device according to claim 1, wherein said at least one metric that characterizes a morphology of a deflection complex in the electrogram signal measured by the signal processing and evaluation unit comprises a metric which measures the complexity of the deflection complex.

13. The device according to claim 1, wherein the signal processing and evaluation unit comprises a deflection detection unit that identifies waveform deflections in the electrogram signal, a parameter measurement unit that measures deflection intervals between each pair of consecutive deflection complexes in the electrogram signal and measures at least one metric that characterizes the morphology of a deflection complex in the electrogram signal, and a parameter evaluation unit that generates a multi-dimensional deflection vector of at least two dimensions for each identified deflection, wherein at least one element is the deflection interval, determines a distance between each pair of consecutive deflections from the multi-dimensional deflection vectors, and determines a cumulative distance between deflections in a time window of predetermined length.

* * * * *